United States Patent [19]

Schwinn et al.

[11] 4,404,187

[45] Sep. 13, 1983

[54] METHOD FOR RENDERING FACTORS II AND VII HEPATITIS-SAFE WITH A CHELATING AGENT

[75] Inventors: Horst Schwinn; Norbert Heimburger, both of Marburg; Gerhardt Kumpe, Wetter; Hans M. Preis, Marburg, all of Fed. Rep. of Germany

[73] Assignee: Behringwerke Aktiengesellschaft, Marburg, Fed. Rep. of Germany

[21] Appl. No.: 323,116

[22] Filed: Nov. 19, 1981

[30] Foreign Application Priority Data

Nov. 21, 1980 [DE] Fed. Rep. of Germany ....... 3043857

[51] Int. Cl.³ ............................................. A61K 35/14
[52] U.S. Cl. .................................................. 424/101
[58] Field of Search ....................................... 424/101

[56] References Cited

U.S. PATENT DOCUMENTS 4,327,086  4/1982  Fukushima et al. ................ 424/101

*Primary Examiner*—Sam Rosen
*Attorney, Agent, or Firm*—Curtis, Morris & Safford

[57] ABSTRACT

What is disclosed is a method for treating a preparation containing blood clotting Factors II and/or VII to render it virtually hepatitis-free by warming said preparation in the presence of a chelating agent and in the further presence of an amino acid and/or a saccharide or sugar alcohol.

5 Claims, No Drawings

METHOD FOR RENDERING FACTORS II AND VII HEPATITIS-SAFE WITH A CHELATING AGENT

The invention relates to a process for the production of a virtually hepatitis-safe preparation of blood-clotting Factors II (prothrombin) and/or VII by warming in the presence of a chelating agent, if appropriate in the presence of an amino acid and/or a saccharide or sugar alcohol.

Blood-clotting is a complex function which proceeds in stages and is initiated by various physiological as well as pathological causes and the course of which depends on about 20 promoting and inhibiting factors. As a result of a reduction or increase in these blood-clotting factors, disorders of blood-clotting arise and some of these manifest themselves as diseases.

Thus, for example, a liver illness with a reduced synthesis performance of this organ leads to a fall in the plasma-prothrombin level (=Factor II level) and the plasma-proconvertin level (=Factor VII level), and this is a process which can lead to spontaneous, life-endangering hemorrhages. In this case, Factor II/VII concentrates are the medicament of choice for a therapy which acts immediately.

A Factor II preparation can be produced by the method of Soulier et al., Thrombos.Diath. Haemorrh. Suppl. 35, 61 (1969).

Such a preparation is not free from the risk of transmitting hepatitis. Albumin is regarded as hepatitis-safe, if it is heated in aqueous solution for 10 hours at 60° C., in the presence of stabilisers [Gellis, S.S. et al., J. Clin. Invest. 27, 239 (1948)]. It may therefore be assumed that a Factor II/VII concentrate which had been heated in the presence of suitable stabilizers is also hepatitis-safe.

German Offenlegungsschrift No. 2,916,711 has disclosed a process for the heat-stabilization of clotting factors in aqueous solution by adding an aminoacid and a monosaccharide or oligosaccharide or a sugar alcohol.

However, even in this way, a considerable loss in yield of Factor II cannot be prevented (Example 4 of the German Offenlegungsschrift). The Factors VII, IX and X, which are usually contained in a Factor II concentrate and are important for the activity of the latter, are completely inactivated under the conditions described.

Thus, there was still the object of discovering a process for the heat-stabilization of aqueous solution of Factor II, in order to reduce the losses in activity.

Surprisingly, it has now been found that an aqueous solution of Factor II and/or Factor VII can be heat-stabilized by the addition of a chelating agent, such as ethylenediaminetetraacetic acid. Hitherto, no process for the stabilization of Factor VII against inactivation by heat was known.

The invention relates to a process for the production of a virtually hepatitis-safe preparation of blood-clotting Factors II and/or VII by warming in the presence of a chelating agent, if appropriate in the presence of an aminoacid and/or a saccharide or sugar alcohol. Examples of chelating agents of this type are: ethylenediaminetetraacetic acid (EDTA), ethylene glycol-bis-(2-aminoethyl ether)-tetraacetic acid (EGTA), diaminocyclohexanetetraacetic acid (CDTA), diaminopropanetetraacetic acid, diaminopropan-2-ol-tetraacetic acid and nitrilotriacetic acid, as well as the soluble metal salts of these.

Preferably, the sodium salts of ethylenediaminetetraacetic acid (EDTA) and ethylene glycol-bis-(2-aminoethyl ether)-tetraacetic acid (EGTA) are used.

In the presence of chelating agents of this type, the aqueous solution of the clotting factors can be heated for such a long period that, according to the present state of knowledge, the transmission of hepatitis pathogens can be virtually excluded. This applies especially in conjunction with precipitation processes in which the active ingredient remains in the supernatant liquid and the hepatitis viruses can be separated off together with the insoluble precipitate. A preparation which has been kept for at least 10 hours at about 60° C. in aqueous solution is nowadays regarded as virtually hepatitis-safe, in particular if the starting material used is human tissue in which hepatitis viruses cannot be detected after a test of the third generation.

The chelating agent is suitably present in the preparation at a concentration from oil mole/liter to 1 mole/liter.

In a particularly preferred embodiment of the invention, 0.01 to 0.3 mole/l of one of the chelating agents listed above, preferably 0.05 to 0.3 mole/l of the Na salt of ethylenediaminetetraacetic acid and, if appropriate, 1.0 to 3.0 moles/l of at least one of the aminoacids glycine, α-or β-alanine, hydroxyproline, proline, glutamine or α-, β- or γ-aminobutyric acid, preferably glycine, and 20 to 60% by weight of monosaccharides or oligosaccharides or sugar alcohols, preferably 1.0 to 3.0 moles/l of glycine and 20 to 60% by weight of sucrose, are added to a solution containing Factor II and/or Factor VII, preferably a plasma fraction or placenta fraction, the mixture is heated to a temperature of between 30° C. and 100° C., preferably 60° C. to 100° C., and held at this temperature for 1 minute to 48 hours, preferably about 10 hours, the shortest time being associated with the highest temperature, and vice versa. To obtain a maximum yield, the pH value must be matched specifically to the individual clotting factors present in the solution. In general, a pH value within the limits of 6.5 and 8.0 should be maintained. A virtually hepatitis-safe preparation of Factor II and/or Factor VII is obtained.

Depending on the solubility of the chelating agent, the aminoacid or the carbohydrate, the values of 0.3 and 3.0 moles/l or 60% by weight respectively can be extended to higher concentrations, if the chelating agent, the aminoacid or the carbohydrate have a correspondingly higher solubility at the desired temperature. The heat treatment can also be carried out in several successive steps.

When the preferred combination of the disodium salt of the ethylenediaminetetraacetic acid with glycine and sucrose is used, a hepatitis-safe preparation is obtained by heating under the following conditions: heating for 10 to 20 hours at 60° to 70° C. in the presence of EDTA-Na$_2$ in a concentration from 0.05 to 0.3 mole/l, of sucrose in a concentration from 40 to 60% by weight and of glycine in a concentration from 1.0 to 2.5 moles/l, at a pH value from 6.8 to 8.0.

Due to the addition of EDTA-Na$_2$, the process according to the invention is superior to that of German Offenlegungsschrift No. 2,916,711. As shown by the table, the stabilization of Factor II is considerably improved, and that of Factor VII would not be possible without it.

TABLE

Effect of EDTA on the stability of the clotting factors

| Stabilizers | Clotting factor (U/ml) | | | |
|---|---|---|---|---|
| | II | | VII | |
| | Before heating | After heating | Before heating | After heating |
| Sucrose 60% by weight Glycine 2 moles/l | 40 | 4 | 20 | 0 |
| EDTA 0.1 mole/l Sucrose 60% by weight Glycine 2 moles/l | 40 | 38 | 20 | 18 |

The recovery and purification of the clotting factors from the heated solution can be carried out by precipitation with 30–45% weight/volume of ammonium sulfate and adsorption of the supernatant liquid on 0.4 to 1.0% weight/volume of Ca phosphate.

Advantageously, the starting fractions are those in which the factor to be stabilized has been enriched according to the cited process.

Due to the knowledge of the methods for the determination of the substances concerned, those skilled in the art are familiar with monitoring the measure for the enrichment and purification of Factor II or VII. Using these monitoring methods, the process conditions can be controlled with regard to a satisfactory yield and a satisfactory purity of the product.

To obtain a hepatitis-safe concentrate of Factor II and/or VII, the starting material used is a fraction such as is obtained, for example, by the process of Soulier et al., Thrombosis Diath. Haemorrh. Suppl. 35, 61 (1969). For this purpose, plasma obtained from blood anticoagulated with 0.01 mole/l of EDTA is adsorbed on Ca phosphate, and the solid is centrifuged off. Thus, the factors are quantitatively bonded to the adsorbent and can be recovered by several elutions with 0.2 mole/l of trisodium citrate. The combined eluates are further purified by combined alcohol and acetic acid precipitations at temperatures and $-8°$ C. to $+4°$ C. At the same time, the factors are thus concentrated.

The concentrate is taken up at a pH of 7.6 in a suitable buffer, preferably sodium chloride/sodium citrate in concentrations of 0.06 and 0.02 mole/l respectively, and the activity of the factors is determined.

Those skilled in the art are familiar with the activity determinations. For Factor II, this can be carried out, for example, by the method of Koller, F. et al., Dtsch.med.Wschr. 81, 516 (1956). For this purpose, one part, for example 0.1 ml, of plasma deficient in Factor II, and one part of diluted normal plasma are mixed. This mixture is kept for 30 seconds at $+37°$ C. Subsequently, two parts of calcium-containing thromboplastin prepared, for example, according to German Patent 2,356,493 are added and the time is determined which elapses until a clot appears. For quantitative data, the clotting time resulting with the solution containing Factor II is read off by reference to a calibration curve obtained with a dilution series of normal plasma.

One unit of Factor II corresponds to the Factor II activity of 1 ml of normal plasma.

Factor VII can be determined, for example, by the method of Koller, F. et al., Acta haemat. 6, 1 (1951). For this purpose, one part, for example 0.1 ml, of plasma deficient in Factor VII, and one part of diluted normal plasma are mixed. This mixture is kept for 30 seconds at $+37°$ C. Subsequently, two parts of calcium-containing thromboplastin, prepared, for example, according to German Pat. No. 2,356,493, are added and the time is determined which elapses until a clot appears. For quantitative data, the clotting time resulting with the solution containing Factor VII is read off by reference to a calibration curve obtained with a dilution series of normal plasma.

One unit of Factor VII corresponds to the Factor VII activity of 1 ml of normal plasma.

To destroy the hepatitis viruses, a chelating agent and glycine and sucrose are added to the solution and the whole is heated.

For further purification, the heated solution is centrifuged if necessary, and impurities are removed by precipitation with 30–45% weight/volume of ammonium sulfate.

The supernatant liquid is adsorbed on 0.04 to 1.0% weight/volume of calcium phosphate, the charged adsorbent is washed and eluted with citrate buffer, and the eluate is dialysed.

For administration to humans, the product is subjected to sterilization by filtration.

The invention particularly relates to a hepatitissafe preparation of Factors II and VII, which is obtainable by this process and is low in protein.

To increase the storage stability, it is advantageous to add protein-stabilizing substances, for example proteins, aminoacids or carbohydrates, to the preparation. Finally, the preparation which has been subjected to this treatment can be made available in a freeze-dried form, and in this case an addition of anticoagulants, such as, for example, heparin, can be advantageous.

In the solution suitable for pharmaceutical administration, the product according to the invention is a medicament for the treatment of coagulopathy, and it can be used intravenously, advantageously as an infusion, for the therapy and prophylaxis of hemmorrhages caused by deficiencies in Factor II and/or Factor VII.

The invention will be explained in more detail by the examples which follow:

EXAMPLE 1

Preparation of a hepatitis-safe concentrate of Factors II/VII from human citrate plasma:

250 g of an anion exchanger (Type A50 Sephadex-DEAE) are added to 500 liters of citrate plasma, and the mixture is stirred for 60 minutes. After sedimentation of the adsorbent, the supernatant plasma is siphoned off and the residue is washed with 20 liters of 0.85% strength NaCl solution.

The adsorbent is eluted with 7.5 liters of 1 mole/l NaCl solution at pH 8.0 and is then discarded. 1.12 kg of glycine, 11.2 kg of sucrose and 143 g of EDTA-Na$_2$ are added to the eluate, and the mixture is heated for 10 hours at 60° C. at pH 7.6.

After cooling, the mixture is diluted with 50 liters of distilled water and brought to an ammonium sulfate concentration of 40% weight/volume. The precipitate is centrifuged off and discarded. 0.5 kg of Ca phosphate are added to the supernatant liquid which is left to stand for 30 minutes at pH 7.6. After centrifuging, the supernatant liquid is discarded and the adsorbent is washed with twice 10 liters of 0.5 mole/l NaCl solution. The adsorbent is eluted with 1.8 liters of buffer of pH 8.0, which contains 0.2 mole/l of trisodium citrate, 0.15 mole/l of NaCl, 2 g/100 ml of glycine, 0.3 U/ml of antithrombin III and 14 IU/ml of heparin. After the addition of 0.2 g/100 ml of colloidal silica as a centrifuging aid, the eluate is separated from the adsorbent by centrifuging at 30,000 g. The residue is discarded and the supernatant liquid is dialyzed for 3 hours against 100 liters of a buffer of pH 7, containing 0.06 mole/l of NaCl, 0.02 mole/l of trisodium citrate and 2 g/100 ml of glycine. The dialyzate is tested for the activity of Factors II and VII, adjusted to the desired concentration, sterilized by filtration, divided into unit doses and lyophilized.

About 250 dosage units, each of 200 units of Factor II, are obtained from 500 liters of plasma.

EXAMPLE 2

Heating of a Factor II complex concentrate, produced by the process of Soulier et al. [Thromb. Diath. Haemorrh., Suppl. 35, 61, 1969], for inactivating the hepatitis viruses:

The lyophilized product from 4 dosage units of Factor II concentrate, each having about 200 units, is taken up in 20 ml of an aqueous solution which contains 2.2 moles/l of glycine, 1 g/ml of sucrose and 800 mg of EDTA-$Na_2$. The pH value is 7.6. After complete dissolution, the container is sealed air-tight and incubated for 10 hours at 60° C. in a water bath. After cooling, the mixture is diluted with 160 ml of distilled water and brought to saturation with 40% weight/volume of ammonium sulfate. The precipitate is centrifuged off and the supernatant liquid is adsorbed on 0.8 g of Ca phosphate.

All the further steps are carried out corresponding to Example 1, taking into account the quantitative ratios which are transferable.

We claim:

1. A method for making a preparation containing at least one member selected from the group consisting of blood clotting Factor II and blood clotting factor VII virtually hepatitis-safe, which method comprises warming said preparation in the presence of an effective amount of a chelating agent and in the further presence of at least one member selected from the group consisting of amino acids, saccharides, and sugar alcohols.

2. A method as in claim 1 wherein said chelating agent is present at a concentration from 0.1 mole/liter to 1 mole/liter.

3. A method as in claim 1 wherein said chelating agent is the sodium salt of ethylenediamine-tetraacetic acid or of ethylene glycol-bis-(2-aminoethyl ether)-tetraacetic acid.

4. A method as in claim 1 wherein said chelating agent is present at a concentration from 0.01 mole/liter to 3.0 moles/liter and said preparation is warmed at 30° C. to 100° C. for 1 minute to 48 hours.

5. A method as in claim 4 wherein said warming is carried out in the additional presence of 1.0 mole/liter to 3.0 moles/liter of at least one amino acid selected from the group consisting of glycine, α-alanine, β-alanine, hydroxyproline, proline, glutamine, and α-, β-, and γ- aminobutyric acids and of 20 to 60 percent by weight of a member selected from the group consisting of monosaccharides, oligosaccharides, and sugar alcohols.

* * * * *